United States Patent
Asama et al.

(10) Patent No.: US 9,987,415 B2
(45) Date of Patent: Jun. 5, 2018

(54) EQUIPMENT MOUNTING APPARATUS AND METHOD OF CONTROLLING EQUIPMENT MOUNTING APPARATUS

(71) Applicant: Terumo Kabushiki Kaisha, Tokyo (JP)

(72) Inventors: Koichiro Asama, Hadano (JP); Shinji Katou, Hadano (JP); Yuuya Tounooka, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 351 days.

(21) Appl. No.: 14/663,267

(22) Filed: Mar. 19, 2015

(65) Prior Publication Data
US 2015/0190567 A1   Jul. 9, 2015

Related U.S. Application Data

(63) Continuation of application No. PCT/JP2012/006215, filed on Sep. 27, 2012.

(51) Int. Cl.
*G06Q 50/00* (2012.01)
*A61M 5/14* (2006.01)
(Continued)

(52) U.S. Cl.
CPC ........ *A61M 5/1415* (2013.01); *A61M 5/1417* (2013.01); *A61M 5/1418* (2013.01);
(Continued)

(58) Field of Classification Search
CPC .................................................. A61M 37/00
See application file for complete search history.

(56) References Cited

U.S. PATENT DOCUMENTS

| | | | | |
|---|---|---|---|---|
| 4,756,706 A | * | 7/1988 | Kerns | A61M 5/1413 128/DIG. 13 |
| 5,713,856 A | * | 2/1998 | Eggers | A61M 5/1413 604/65 |

(Continued)

FOREIGN PATENT DOCUMENTS

| | | |
|---|---|---|
| EP | 0 960 627 A2 | 12/1999 |
| EP | 2 623 141 | 8/2013 |

(Continued)

OTHER PUBLICATIONS

Extended European Search Report issued in corresponding application No. 12885891.7 dated Apr. 12, 2016.
(Continued)

*Primary Examiner* — Robert A Sorey
(74) *Attorney, Agent, or Firm* — Foley & Lardner LLP

(57) ABSTRACT

An equipment mounting apparatus on which a plurality of equipment devices are mountable, each equipment device having, in a memory thereof, drug dosage information associated with drug usage location information, includes a main body having a plurality of installation portions, each installation portion being configured to receive one of the equipment devices. Each of the equipment devices is configured such that, when the drug usage location information is specified, the equipment device displays the related drug dosage information based on the drug usage location information that is specified. The equipment mounting apparatus is configured to set a standard specifying drug usage location information and to use the standard specifying drug usage location information to cause the drug usage location information of each of the plurality of equipment devices to coincide with the standard specifying drug usage location information.

8 Claims, 9 Drawing Sheets

(51) Int. Cl.
*G09F 3/00* (2006.01)
*G06F 19/00* (2018.01)

(52) U.S. Cl.
CPC ........... *G09F 3/00* (2013.01); *A61M 2205/50* (2013.01); *A61M 2205/60* (2013.01); *A61M 2205/6018* (2013.01); *A61M 2205/6054* (2013.01); *G06F 19/3468* (2013.01)

(56) References Cited

U.S. PATENT DOCUMENTS

| | | | | |
|---|---|---|---|---|
| 2002/0134570 | A1* | 9/2002 | Franklin-Lees | A61M 5/1413 174/58 |
| 2007/0219495 | A1* | 9/2007 | Kato | A61M 5/1413 604/131 |
| 2009/0177188 | A1* | 7/2009 | Steinkogler | A61M 5/1413 604/890.1 |
| 2011/0028885 | A1* | 2/2011 | Eggers | A61M 5/1413 604/19 |
| 2012/0185267 | A1* | 7/2012 | Kamen | G06Q 50/22 705/2 |
| 2014/0046296 | A1* | 2/2014 | Clarke | A61M 5/1456 604/507 |
| 2014/0321096 | A1* | 10/2014 | Kajackas | A61G 12/00 361/807 |
| 2015/0041419 | A1* | 2/2015 | Hasegawa | A61M 5/1413 211/85.13 |
| 2015/0224252 | A1* | 8/2015 | Borges | A61M 5/142 700/282 |

FOREIGN PATENT DOCUMENTS

| | | |
|---|---|---|
| JP | 11-347118 | 12/1999 |
| JP | 2005-506103 | 3/2005 |
| JP | 2008-167888 A | 7/2008 |
| JP | 2011-087678 | 5/2011 |
| JP | 2012-070991 | 4/2012 |
| JP | 2012-161531 | 8/2012 |
| WO | WO-02/069099 A2 | 9/2002 |
| WO | WO-2012/042763 A1 | 4/2012 |
| WO | WO-2012/065649 A1 | 5/2012 |
| WO | WO-2012/108147 | 8/2012 |

OTHER PUBLICATIONS

International Search Report in PCT/JP2012/006215 dated Jan. 15, 2013.
Communication issued in EP Patent application No. EP 12885891.7 dated Oct. 12, 2017.

* cited by examiner

EQUIPMENT MOUNTING APPARATUS AND METHOD OF CONTROLLING EQUIPMENT MOUNTING APPARATUS

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2012/006215 filed on Sep. 27, 2012, the entire contents of which is hereby incorporated by reference in its entirety.

BACKGROUND

Technical Field

The present disclosure relates to an equipment mounting apparatus and a method of controlling an equipment mounting apparatus such as a rack device or the like in which medical equipment or the like such as an infusion pump or the like used at hospitals or the like is mounted, for example.

Background Art

In the related art, in a case of dosing a patient or the like with a drug solution in a hospital and the like, when a dose needs to be precisely controlled, for example, an infusion pump is employed(for example, see JP-A-2011-87678).

When such an infusion pump or the like is employed in hospitals, sometimes a plurality of pumps are used, as one pump may not be sufficient.

In such a case, an equipment mounting apparatus, for example, a rack device or the like is used in which a plurality of the infusion pumps or the like can be mounted.

For example, in one rack device, the plurality of infusion pumps, for example three infusion pumps, are mounted, thereby dosing a patient with drug.

Such an infusion pump or the like has a drug library including data of drugs and the like used at a location where the infusion pump is arranged (a profile, for example, an intensive care unit (ICU)).

Therefore, the infusion pump is configured to be able to utilize the data of the drug library of the infusion pump when an operator inputs the profile which is the location of usage.

Accordingly, when three infusion pumps are mounted in the rack device, an operator such as a nurse or the like sets the profile or the like for each infusion pump.

However, there has been a problem in that it is harsh for a busy nurse or the like to be required to perform the aforementioned operation.

Moreover, there has been another problem in that if setting is erroneously performed when setting a profile for each infusion pump and the like, data of a drug library included in the infusion pump and the like cannot be used properly.

SUMMARY OF INVENTION

One objective of certain embodiments of the present invention is to provide an equipment mounting apparatus in which drug usage location information, such as a profile or the like, in each of a plurality of sets of equipment, such as an infusion pump or the like, is prevented from being erroneously input, in which the drug usage location information of the mounted equipment is unified, and in which drug related information such as a drug library or the like included in the equipment can be effectively utilized. An object of certain embodiments of the present invention is also to provide a method of controlling an equipment mounting apparatus.

According to one embodiment, an equipment mounting apparatus on which a plurality of equipment devices are mountable, each equipment device having, in a memory thereof, drug dosage information associated with drug usage location information, includes a main body having a plurality of installation portions, each installation portion being configured to receive one of the equipment devices. Each of the equipment devices is configured such that, when the drug usage location information is specified, the equipment device displays the related drug dosage information based on the drug usage location information that is specified. The equipment mounting apparatus is configured to set a standard specifying drug usage location information and to use the standard specifying drug usage location information to cause the drug usage location information of each of the plurality of equipment devices to coincide with the standard specifying drug usage location information.

According to the above-described configuration, the equipment mounting apparatus generates the standard specifying drug usage location information (for example, the specified drug usage location information, such as ICU or the like, of a first mounted infusion pump) as a single item of the specified drug usage location information (for example, ICU) and uses the standard specifying drug usage location information to cause the drug usage location information of each of the equipment devices (for example, an infusion pump or the like) to coincide with the standard specifying drug usage location information.

Therefore, because the items of the drug usage location information of the infusion pumps and the like mounted in the same equipment mounting apparatus, for example a rack device, are unified, it is possible to appropriately utilize the drug related information such as a drug library or the like in each infusion pump and the like.

Moreover, because there is no need for an operator to input the drug usage location information for each infusion pump or the like, for example, it is possible to lighten the labor thereof and to prevent an erroneously performed input or the like.

Therefore, it is possible to prevent an occurrence of a situation in which the drug related information such as the drug library or the like cannot be effectively utilized due to the erroneously performed input or the like.

In one aspect, the equipment mounting apparatus is configured such that, after the standard specifying drug usage location information is used to cause the drug usage location information of each set of the equipment devices to coincide with the standard specifying drug usage location information, when there is a change in the drug usage location information of one of the plurality of the equipment devices to a post-change drug usage location information, the equipment mounting apparatus changes the drug usage location information of the other or others of the plurality of equipment devices is changed to coincide with the post-change drug usage location information.

According to the aforementioned configuration, after the standard specifying drug usage location information is used to cause the drug usage location information of each set of the equipment to coincide with the standard specifying drug usage location information, when there is a change in the drug usage location information of the equipment, the drug usage location information of other sets of the equipment is configured to coincide with the post-change specified drug usage location information in which the change is made.

Therefore, after the equipment such as the infusion pump or the like is mounted in the equipment mounting apparatus such as the rack device or the like and the dosing of the drug starts, for example, if a change is made in the drug usage location information (for example, ICU) of one equipment by an operator due to another item of the drug usage location information (for example, an emergency room (ER)) for some reason, the drug usage location information of the other sets of the equipment is configured to coincide with the post-change specified drug usage location information (for example, ER) upon detection of the change.

Accordingly, after the specified drug usage location information (ICU) of each set of the equipment is unified, even though another change is made in a portion thereof causing the drug usage location information to be inconsistent, it is possible to cause the drug usage location information (ER) to coincide therewith promptly and automatically.

Therefore, even though a change is made in the specified drug usage location information, there is no need for a nurse and the like such as an operator to manually change the drug usage location information of all the equipment every time the change occurs, for example.

In one aspect, the equipment mounting apparatus is configured to set the standard specifying drug usage location information as the drug usage location information of a first mounted equipment device among the equipment devices.

In one aspect, the equipment mounting apparatus is configured to set the standard specifying drug usage location information as a specified drug usage location information associated with the equipment mounting apparatus.

In one aspect, the specified drug usage location information associated with the equipment mounting apparatus is preloaded in the equipment mounting apparatus.

In one aspect, the standard specifying drug usage location information is the drug usage location information of an equipment device mounted in a predetermined one of the installation portions.

In one aspect, the installation portions are mounted one above the other, and the predetermined one of the installation portions is a top one of the installation portions.

In another embodiment, a method of controlling an equipment mounting apparatus on which a plurality of equipment devices are mountable, each equipment device having, in a memory thereof, drug dosage information associated with drug usage location information, includes determining whether a first equipment device is installed in the equipment mounting apparatus; determining whether a second equipment device is installed in the equipment mounting apparatus; comparing a standard specifying drug usage location information with a drug usage location information of the second equipment device; and, when the standard specifying drug usage location information and the drug usage location information of the second equipment device are not the same, changing the drug usage location information of the second equipment device to match the standard specifying drug usage location information.

In one aspect, the method further comprises acquiring a drug usage location information of the first equipment device; and storing the drug usage location information of the first equipment device as the standard specifying drug usage location information.

In one aspect, the first equipment device is an equipment device that is installed in the equipment mounting apparatus before the second equipment device is installed in the equipment mounting apparatus In one aspect, the first equipment device is an equipment device that is installed in a predetermined installation portion of the equipment mounting apparatus.

In one aspect, the standard specifying drug usage location information is a predetermined drug usage location information associated with the equipment mounting apparatus.

In one aspect, the method further comprises, after a drug usage location information of each of the plurality of equipment devices is changed to match the standard specifying drug usage location information, when there is a change in the drug usage location information associated with one of the plurality of equipment devices to a post-change drug usage location information, changing the drug usage location information associated with each of the others of the plurality of equipment devices to match the post-change drug usage location information.

As described above, according to certain embodiments of the present invention, an equipment mounting apparatus is provided in which drug usage location information such as a profile or the like in each of a plurality of sets of equipment such as an infusion pump or the like is prevented from, for example, being erroneously input, in which the drug usage location information of the mounted equipment is unified, and in which drug related information such as a drug library or the like included in the equipment can be effectively utilized. Certain embodiments of the present invention can also provide a method of controlling an equipment mounting apparatus.

DETAILED DESCRIPTION

Hereinafter, preferable embodiments of the invention will be described in detail with reference to the accompanied drawings.

Because the below-described embodiments are preferable specification examples of the present invention, the embodiments are applied with various types of limitation which are technically preferable. However, the scope of the present invention is not limited to the aspects thereof.

First Embodiment

Figure 1:
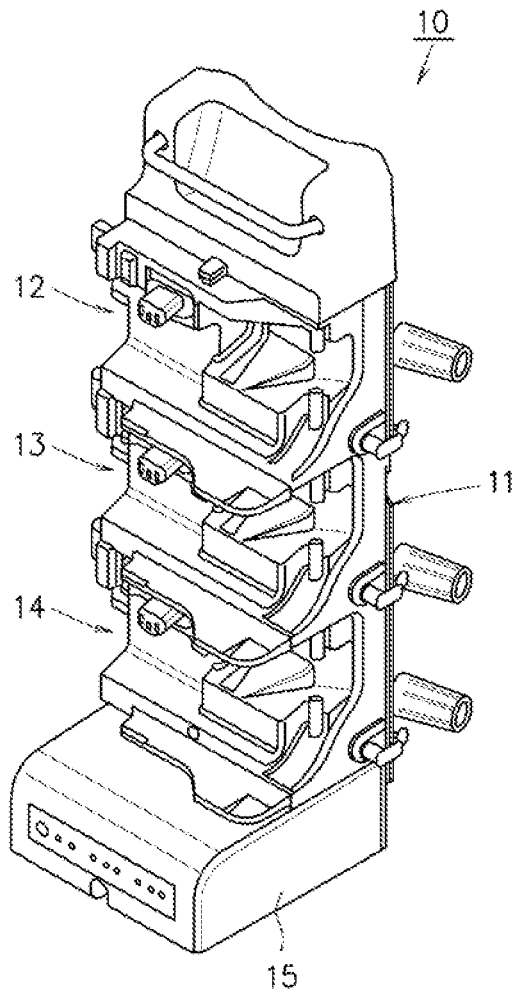
FIG. 1 is a schematic perspective view illustrating a first embodiment of an equipment mounting apparatus of the present invention, for example, a rack device.

FIG. 1 is a schematic perspective view illustrating a first embodiment of an equipment mounting apparatus of the present invention, for example, a rack device 10. As illustrated in FIG. 1, the rack device 10 includes a rack main body 11 and a communication box 15 that is provided at the bottom. As illustrated in FIG. 1, the rack main body 11 has three installation portions, for example, in each of which the equipment, for example, an infusion pump 100 is installed. For example, as illustrated in FIG. 1, the rack main body 11 has a first infusion pump installation portion 12, a second infusion pump installation portion 13, and a third infusion pump installation portion 14.

Figure 2:
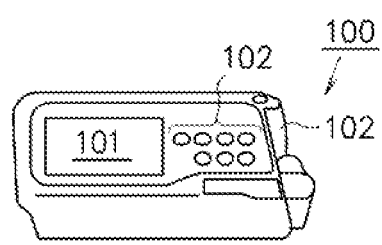
FIG. 2 is a schematic diagram illustrating an infusion pump.

FIG. 2 is a schematic diagram illustrating the infusion pump 100. The infusion pump 10 is configured to have an inside in which a tube and the like for delivering a drug solution can be arranged. In this configuration, the tube is pressurized, for example, and is subjected to a stroke operation or the like, thereby controlling a flow rate of a drug solution delivered through the tube.

As illustrated in FIG. 2, the infusion pump 100 has a display portion, for example, a display 101 configured to be able to display various types of information such as a flow rate of a drug solution or the like. The infusion pump 100 has an input device 102. As illustrated in FIG. 2, the input device 102 has switches such as buttons or the like arranged on the front surface thereof and a dial or the like formed on a side surface thereof The rack device 10 illustrated in FIG. 1 is configured to allow three infusion pumps 100 to be respectively installed in the first infusion pump installation portion 12, the second infusion pump installation portion 13, and the third infusion pump installation portion 14. Accordingly, the rack device 10 is configured to allow three infusion pumps 100, for example, to be mounted and installed to be in use if one infusion pump 100 is insufficient for the dosage when dosing a patient with the drug.

The rack device 10 illustrated in FIG. 1 and the infusion pump 100 illustrated in FIG. 2 respectively have computers. Each computer has a central processing unit (CPU), a random access memory (RAM), a read only memory (ROM), and the like which are not illustrated, and these are connected to one another through a bus.

Figure 3:
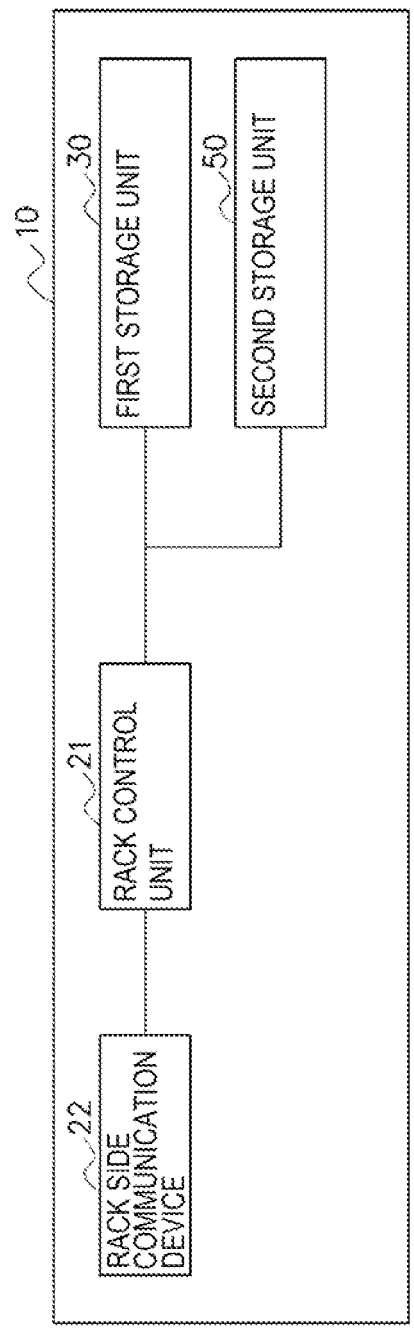
FIG. 3 is a schematic block diagram illustrating a configuration of the rack device of FIG. 1.

FIG. 3 is a schematic block diagram illustrating a configuration of the rack device 10 of FIG. 1. As illustrated in FIG. 3, the rack device 10 has a rack control unit 21. The rack control unit 21 is configured to control a rack side communication device 22 provided for communicating with the infusion pump 100 and the like installed in the rack device 10 and to control a first storage unit 30 and a second storage unit 50 of FIG. 3.

Figure 4:
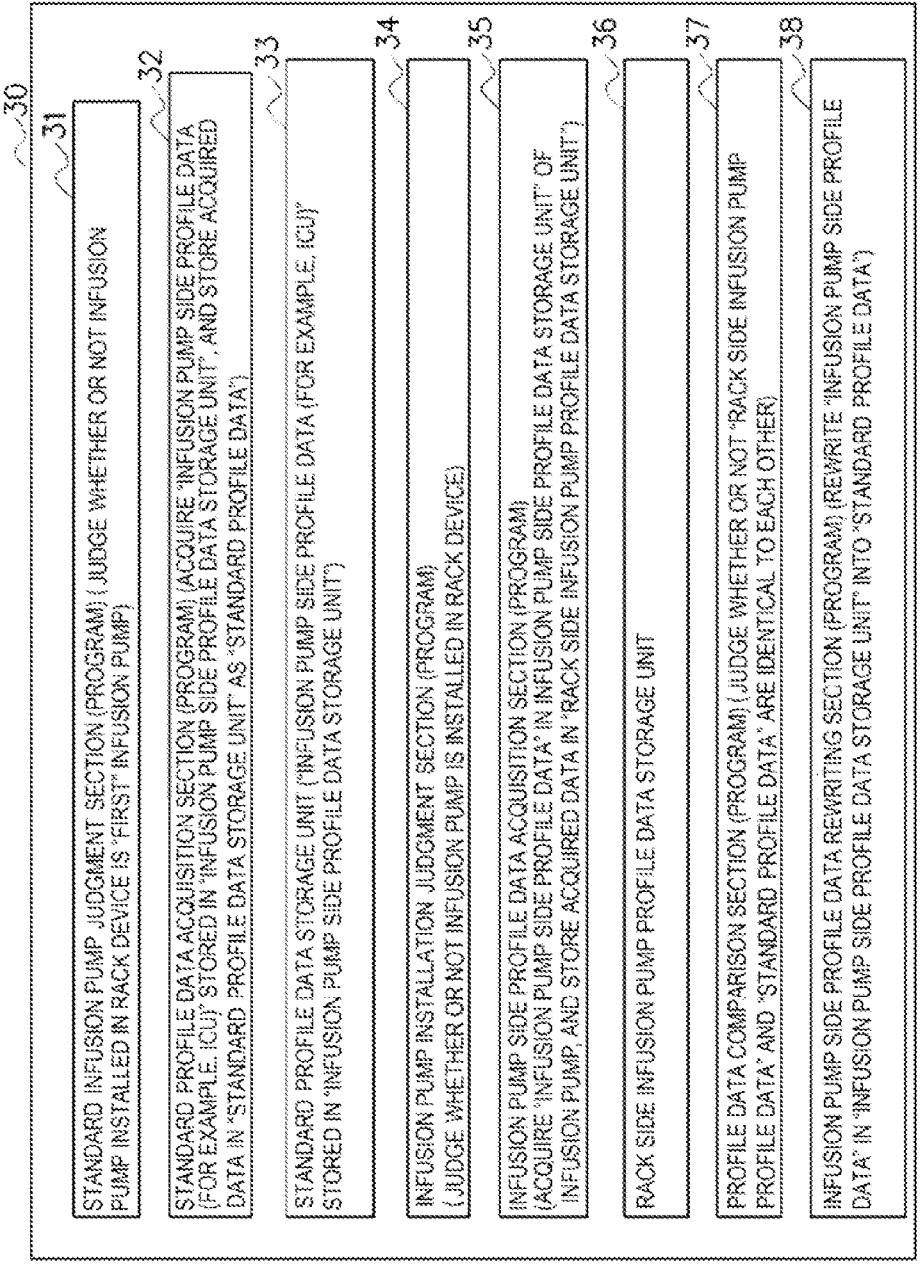
FIG. 4 is a schematic block diagram illustrating contents of a first storage unit of FIG. 3.
Figure 5:
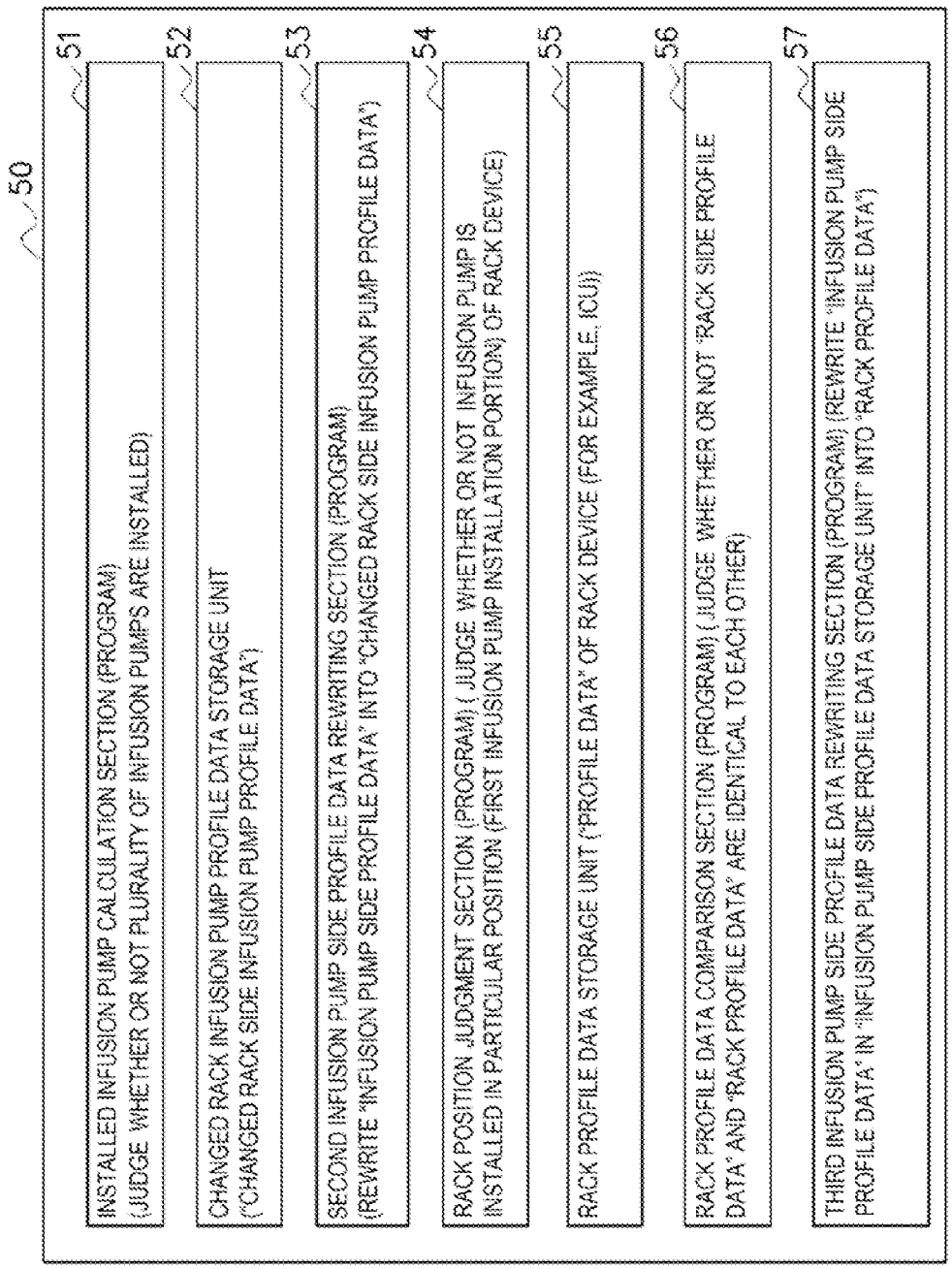
FIG. 5 is a schematic block diagram illustrating contents of a second storage unit of FIG. 3.

FIG. 4 is a schematic block diagram illustrating contents of the first storage unit 30 of FIG. 3, and FIG. 5 is a schematic block diagram illustrating contents of the second storage unit 50 of FIG. 3. Specific descriptions thereof will be given later. For convenience of description, FIG. 5 includes configurations of other embodiments besides the present embodiment.

Figure 6:
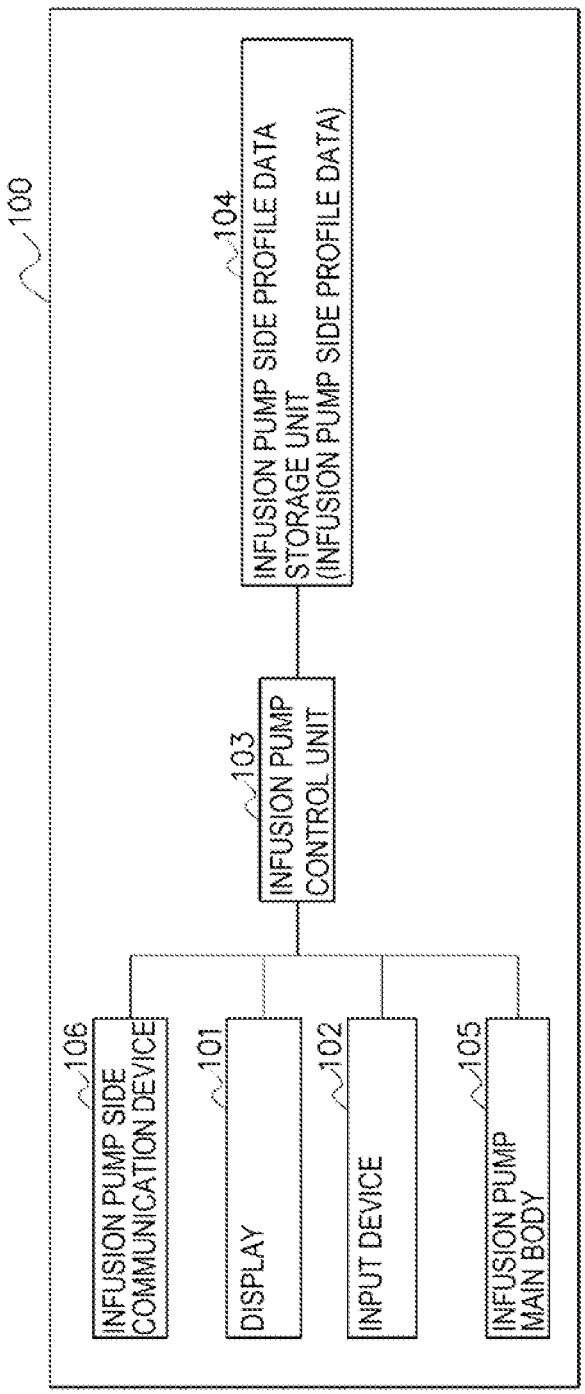
FIG. 6 is a schematic block diagram illustrating a configuration of the infusion pump of FIG. 2.

FIG. 6 is a schematic block diagram illustrating a configuration of the infusion pump 100 of FIG. 2. As illustrated in FIG. 6, the infusion pump 100 has an infusion pump control unit 103. The infusion pump control unit 103 controls an infusion pump main body 105 which is in charge of basic operations or the like for the infusion pump 100 as well as controlling the above-described display 101 and input device 102 together with an infusion pump side communication device 106 and the like. The infusion pump control unit 103 is configured to control an infusion pump side profile data storage unit 104 and the like illustrated in FIG. 6 as well.

Descriptions will be given regarding profile data stored in the infusion pump side profile data storage unit 104.

The infusion pump 100 has information not only on the name of the drug to be used but also on dosage limit values (a hard-limit and a soft-limit) of the drug or the like in accordance with a usage location thereof, for example, an intensive care unit (ICU) or the like. The information is referred to as a "drug library", and such drug information is stored in association with usage location information which is referred to as a "profile".

Accordingly, a nurse or the like using the infusion pump 100 can read out data of the drug library so as to display it on the display 101, for example, by selecting data of the usage location (ICU or the like), and the infusion pump 100 is configured to be able to promptly and easily set a dose (a dosing rate) or the like of the drug with respect to a patient.

In this manner, the profile is an example of drug usage location information, and the drug library is an example of drug related information. The dose limit of drug (a hard-limit and a soft-limit) is an example of drug dosage information.

Specific descriptions for the infusion pump side profile data storage unit 104 of FIG. 6 will be given later.

Figure 7:
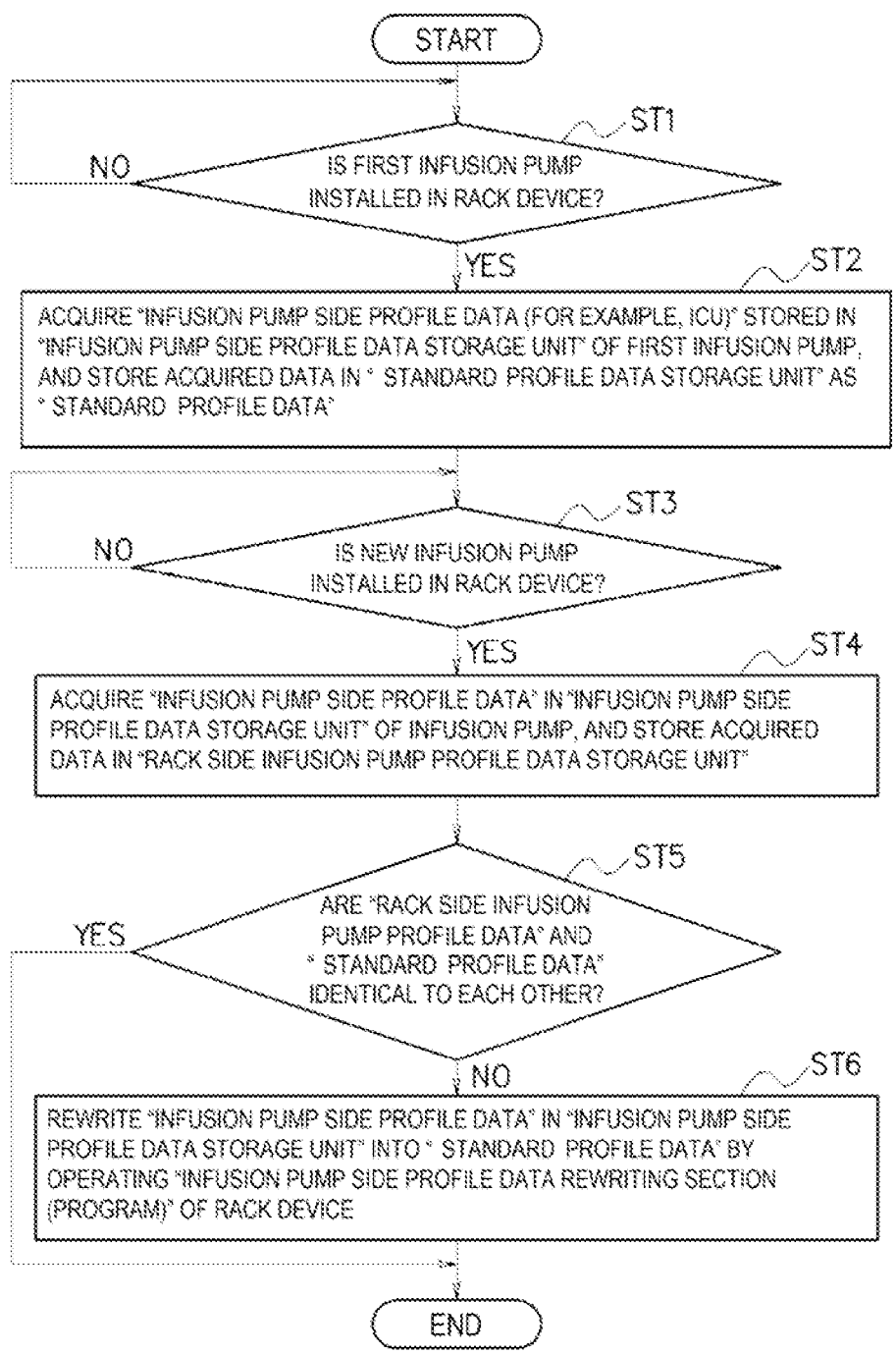
FIG. 7 is a schematic flowchart illustrating operations and the like of the rack device and the infusion pump of the present embodiment.
Figure 8:
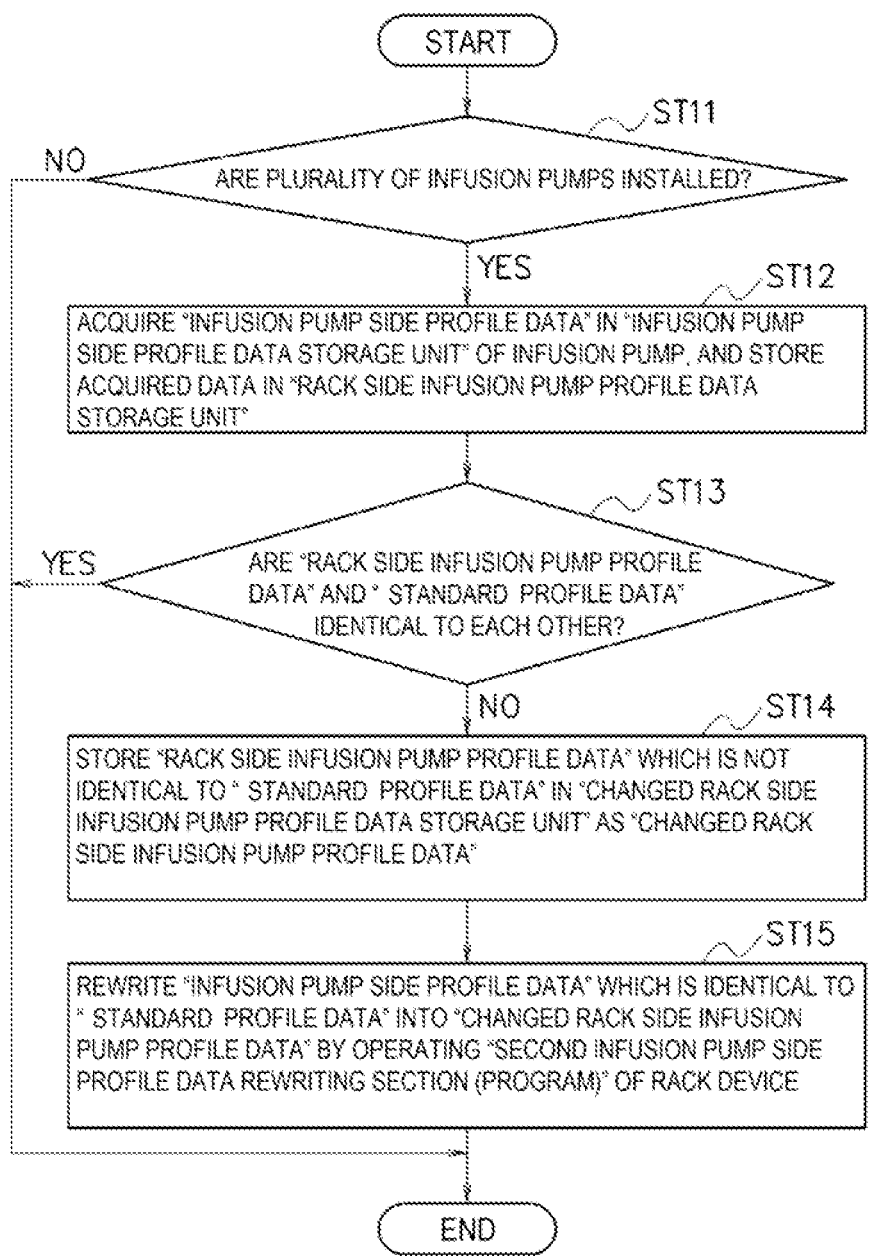
FIG. 8 is another schematic flowchart illustrating operations and the like of the rack device, the infusion pump and the like of the present embodiment.

FIGS. 7 and 8 are schematic flowcharts illustrating operations and the like of the rack device 10, the infusion pump 100, and the like of the present embodiment.

In the present embodiment, descriptions will be given with reference to an example in which an operator, such as a nurse, of the rack device 10, the infusion pump 100, and the like carries the rack device 10 to the intensive care unit (ICU), for example, and installs three infusion pumps 100.

First, a procedure proceeds to step ST (hereinafter, referred to as ST) 1 of FIG. 7. In ST 1, the standard infusion pump judgment section (a program) 31 of FIG. 4 is operated so as to judge whether or not a first infusion pump 100 is installed in the rack device 10.

In ST 1, when it is judged that the first infusion pump 100 is installed in the rack device 10, the procedure proceeds to ST 2.

In ST 2, a standard profile data acquisition section (a program) 32 of FIG. 4 is operated so as to acquire infusion pump side profile data stored in the infusion pump side profile data storage unit 104 of the infusion pump 100 of FIG. 6, with reference thereto.

The infusion pump side profile data is profile data, for example, ICU specified by a nurse or the like operating the infusion pump 100. Accordingly, the infusion pump side profile data is an example of specified drug usage location information.

In ST 2, the infusion pump side profile data (ICU) acquired from the infusion pump 100 is stored in the standard profile data storage unit 33 of FIG. 4 as standard profile data. The standard profile data is an example of standard specifying drug usage location information.

Subsequently, the procedure proceeds to ST 3. In ST 3, an infusion pump installation judgment section (the program) 34 of FIG. 4 is operated so as to judge whether or not a new infusion pump 100 is installed in the rack device 10. In ST 3, when it is judged that the new infusion pump 100 is installed in the rack device 10, the procedure proceeds to ST 4.

In ST 4, an infusion pump side profile data acquisition section (the program) 35 of FIG. 4 is operated so as to acquire the infusion pump side profile data, for example, an emergency room (ER), of the infusion pump side profile data storage unit 104 of FIG. 3 in the newly installed infusion pump 100, thereby storing the ER profile data in the rack side infusion pump profile data storage unit 36 of FIG. 4.

Subsequently, the procedure proceeds to ST 5. In ST 5, a profile data comparison section (the program) 37 of FIG. 4 is operated so as to compare the profile data, for example, the ER profile data stored in the rack side infusion pump profile data storage unit 36 of FIG. 4 and the profile data, for example, the ICU profile data in the standard profile data storage unit 33 of FIG. 4, thereby judging whether or not the two items of the profile data are identical to each other.

In ST 5, when it is judged that the two items of the profile data are not identical, the procedure proceeds to ST 6. In the present embodiment, the two items of the profile data of the ER and the ICU are not identical to each other, and the procedure proceeds to ST 6.

In ST 6, an infusion pump side profile data rewriting section (the program) 38 of FIG. 4 is operated so as to rewrite the infusion pump side profile data of the infusion pump side profile data storage unit 104 of the new infusion pump 100 of FIG. 3, for example, the ER into the standard profile data, for example, the ICU, thereby making a change. In other words, the infusion pump side profile data of the new infusion pump 100 becomes the ICU.

As described above, in the present embodiment, in the same rack device 10, for example, the profile of the second installed infusion pump 100 is unified with the profile of the first installed infusion pump 100 so as to be identical to each other, and the unification is performed automatically. Accordingly, if a nurse or the like operating the rack device 10 and the like sets the profile (for example, the ICU) of the infusion pump 100 when installing the first infusion pump 100; thereafter, the infusion pump 100 installed in the same rack device 10 is automatically set to have the same profile (for example, the ICU) even though no operation is performed by the nurse or the like.

Therefore, it is possible to lighten the labor of the nurse or the like and to prevent the profile from, for example, being erroneously input by the nurse or the like. Thus, information of the drug library included in each infusion pump 100 can be effectively utilized.

The infusion pump 100 which is third installed in the rack device 10 is also similarly processed.

Hereinafter, descriptions will be given with reference to the flowchart of FIG. 8 regarding operations of the rack device 10 and the like when the rack device 10 is moved to another room (another profile, for example, the ER) after the profiles of a plurality, for example, three of the infusion pumps 100 installed in the rack device 10 are set to, for example, the ICU.

First, the procedure proceeds to ST 11 of FIG. 8. In ST 11, an installed infusion pump calculation section (a program) 51 of FIG. 5 is operated so as to judge whether or not a plurality of infusion pumps 100 are installed in the rack device 10. In ST 11, when it is judged that a plurality of infusion pumps 100 are installed in the rack device 10, the procedure proceeds to ST 12.

In ST 12, the infusion pump side profile data acquisition section (the program) 35 of FIG. 4 is operated so as to acquire the infusion pump side profile data in the infusion pump side profile data storage unit 104 of FIG. 3 of the plurality of infusion pumps 100 installed in the rack device 10, thereby storing the data in the rack side infusion pump profile data storage unit 36 of FIG. 4.

Subsequently, the procedure proceeds to ST 13. In ST 13, the profile data comparison section (the program) 37 of FIG. 4 is operated so as to compare rack side infusion pump profile data and the standard profile data of the standard profile data storage unit 33 of FIG. 4, thereby judging whether or not the two items of the profile data are identical to each other. In ST 13, in a case where the rack side infusion pump profile data and the standard profile data acquired from all of the infusion pumps 100 are identical to each other, it is judged that no change has been made.

Meanwhile, in a case where the rack side infusion pump profile data and the standard profile data acquired from any one of the infusion pumps 100 are not identical to each other, it is judged that a change (for example, a change from the ICU to the ER) has been made in the profile data of the infusion pump 100 thereof. Then, assuming that the profile of the infusion pump 100 is changed by a nurse or the like, the procedure proceeds to ST 14.

In ST 14, post-change rack side infusion pump profile data of the infusion pump 100 judged to be subjected to a change in ST 13, for example, the ER is stored in a changed rack infusion pump profile data storage unit 52 of FIG. 5.

Subsequently, the procedure proceeds to ST 15. In ST 15, a second infusion pump side profile data rewriting section (a program) 53 of FIG. 5 is operated so as to rewrite the infusion pump side profile data of the unchanged infusion pump 100, for example, the ICU into the ER, which is the changed rack infusion pump profile data, thereby processing the change.

Accordingly, the items of the infusion pump side profile data of the plurality of infusion pumps 100 in the same rack device 10 are automatically unified to be the ER, for example. In this manner, as a nurse or the like moves the rack device 10 from the ICU to the ER and only changes the profile (the infusion pump side profile data) of one infusion pump 100 thereof to the ER, which is the destination, the items of the infusion pump side profile data of other infusion pumps 100 installed in the same rack device 10 are also changed to the same ER profile data. Accordingly, it is possible to greatly lighten labor of the nurse and the like as an operator of the rack device 10 and the like and to prevent an erroneous operation when changing the profile (from the ICU to the ER).

Second Embodiment

Figure 9:
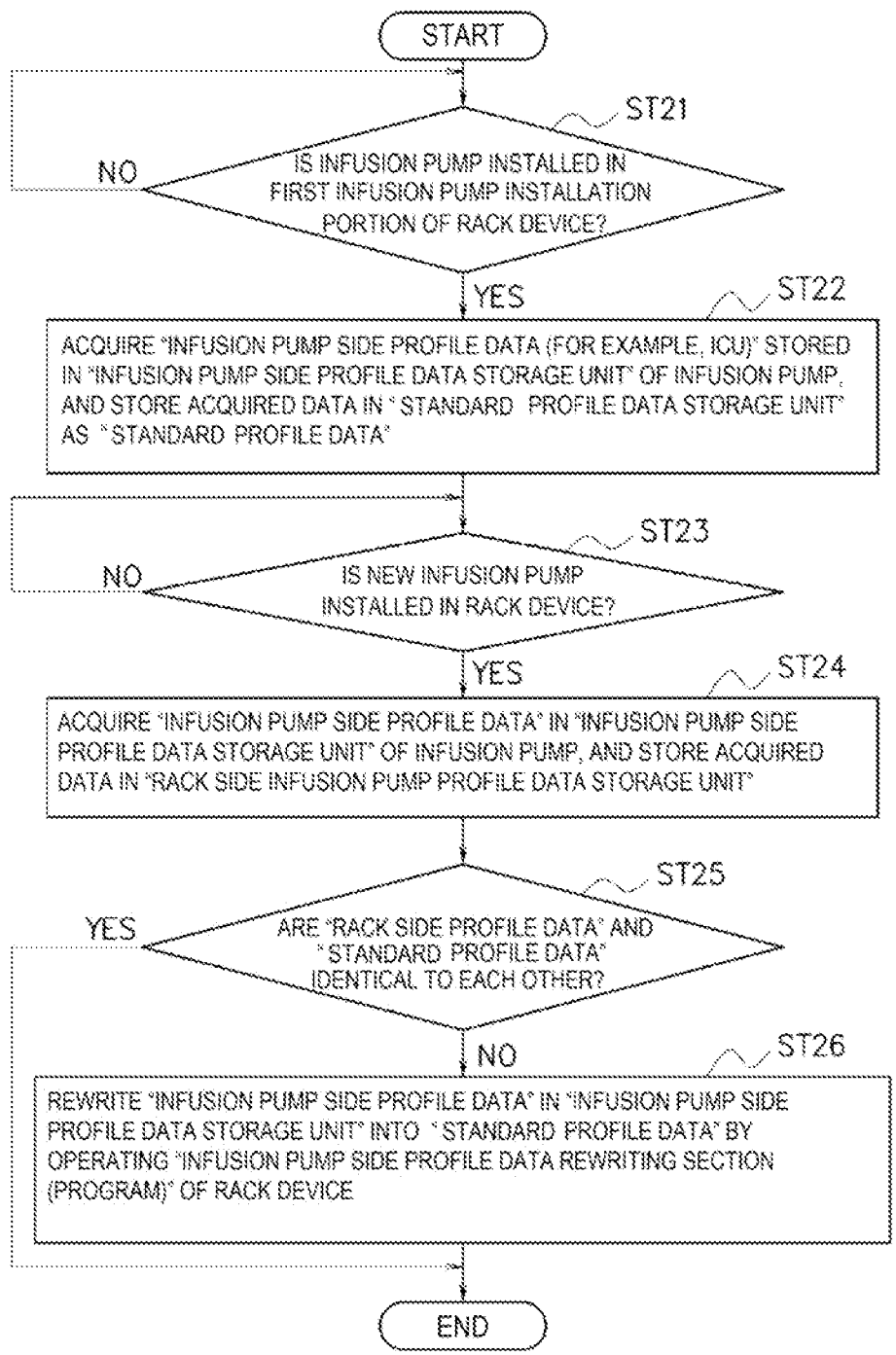
FIG. 9 is a schematic flowchart illustrating operations and the like of the rack device, the infusion pump, and the like of a second embodiment of the present invention.

FIG. 9 is a schematic flowchart illustrating operations and the like of the rack device 10, the infusion pump 100, and the like of a second embodiment of the present invention. Operations and the like of the rack device 10 or the like of the present embodiment are in common with the operations and the like of the above-described first embodiment in many portions. Hereinafter, descriptions will be given mainly focusing on the differences.

In the above-described first embodiment, the infusion pump side profile data of the infusion pump side profile data storage unit 104 in the infusion pump 100 which is first installed in the rack device 10, for example, the ICU is caused to be the standard profile data, thereby processing the infusion pump side profile data of other infusion pumps 100 so as to be unified with this data as well.

In contrast, the present embodiment has a difference in that the infusion pump side profile data in the infusion pump side profile data storage unit 104 of the infusion pump 100 installed in the first infusion pump installation portion 12 of FIG. 1 which is at a particular position of the rack device 10, for example, on the top of the rack device 10 is caused to be the standard profile data, in place of the infusion pump 100 which is first installed in the rack device 10, thereby processing the infusion pump side profile data of other infusion pumps 100 so as to be unified with this data as well.

Hereinafter, specific descriptions will be given.

In ST 21 of FIG. 9, a rack position judgment section (a program) 54 of FIG. 5 is operated so as to judge whether or not the infusion pump 100 is installed at a particular position of the rack device 10, for example, in the first infusion pump installation portion 12 of FIG. 1.

In ST 21, when it is judged that the infusion pump 100 is installed in the first infusion pump installation portion 12, the infusion pump side profile data in the infusion pump side profile data storage unit 104 of the infusion pump 100 is caused to be the standard profile data, thereby causing the infusion pump side profile data of other infusion pumps 100 to be unified with this data as well.

Specifically, the difference between the first and second embodiment is in ST 21, while ST 22 to ST 26 of FIG. 9 of the second embodiment are similar to ST 2 to ST 6 of the first embodiment.

In the present embodiment, as a nurse or the like acting as an operator only sets data of the profile of the infusion pump 100 installed in the first infusion pump installation portion 12 which is on the top of the rack device 10, data of the profiles of other infusion pumps 100 is also automatically changed. Therefore, it is possible to lighten the labor of the nurse or the like and to prevent the profile from, for example, being erroneously input by the nurse or the like. Thus, information of the drug library included in each infusion pump 100 can be effectively utilized.

Third Embodiment

Figure 10:
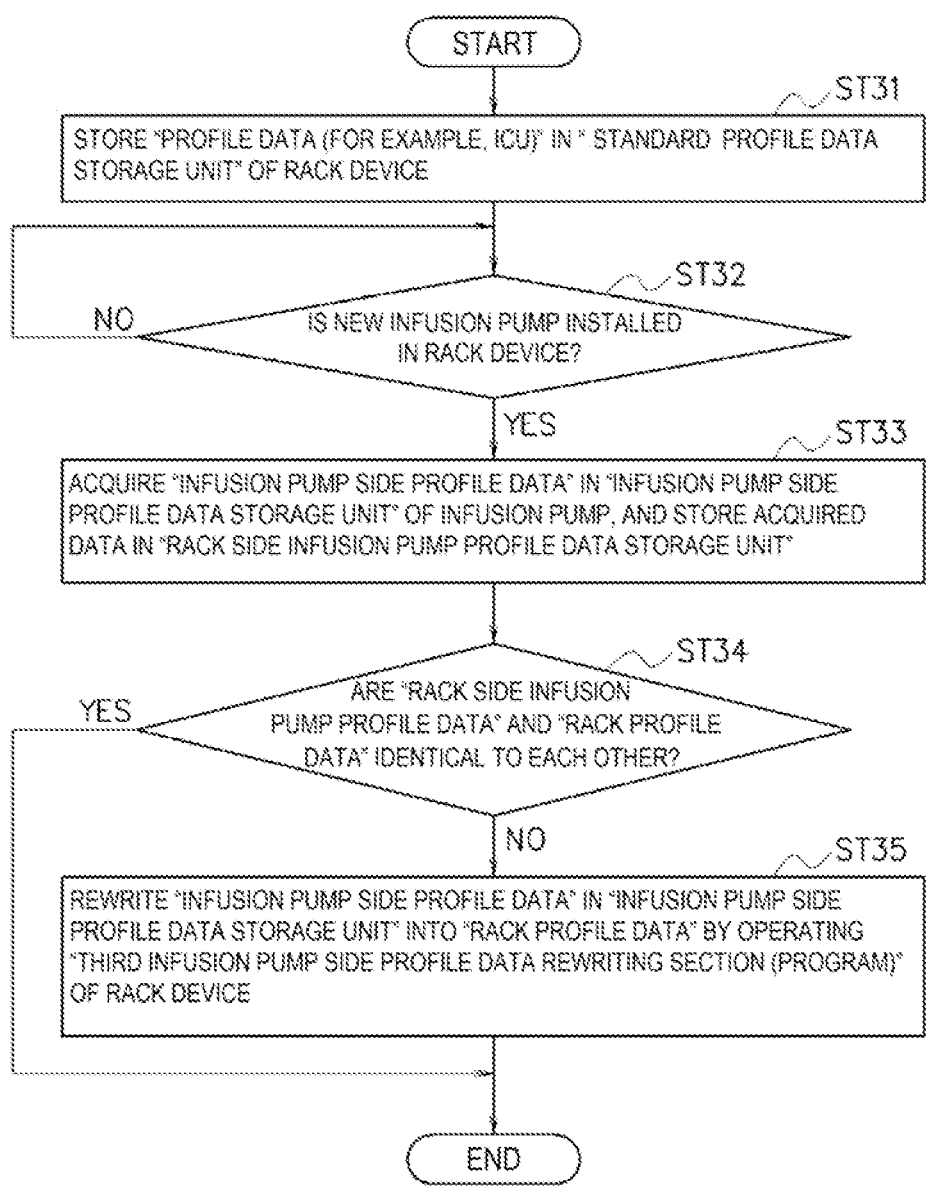
FIG. 10 is a schematic flowchart illustrating operations and the like of the rack device, the infusion pump, and the like of a third embodiment of the present invention.

FIG. 10 is a schematic flowchart illustrating operations and the like of the rack device 10, the infusion pump 100, and the like of a third embodiment of the present invention. Operations and the like of the rack device 10 or the like of the present embodiment are in common with the operations and the like of the above-described first embodiment in many portions. Hereinafter, descriptions will be given mainly focusing on the differences.

In the above-described first embodiment, the infusion pump side profile data of the infusion pump side profile data storage unit 104 in the infusion pump 100 which is first installed in the rack device 10, for example, the ICU is caused to be the standard profile data, thereby processing the infusion pump side profile data of other infusion pumps 100 so as to be unified with this data as well.

In contrast, the present embodiment has a difference in that the profile data as a standard is previously stored in the rack device 10. Then, the profile data stored in the rack device 10 is caused to be the standard, thereby processing the infusion pump side profile data of other infusion pumps 100 so as to be unified with this data as well.

Hereinafter, specific descriptions will be given.

In ST 31 of FIG. 10, first, the profile of a location where the rack device 10 is arranged, for example, the ICU is previously stored in the rack device 10. Specifically, the profile is stored in a rack profile data storage unit 55 of FIG. 5.

Subsequently, the procedure proceeds to ST 32. In ST 32, the infusion pump installation judgment section (the program) 34 of FIG. 4 is operated so as to judge whether or not a new infusion pump 100 is installed in the rack device 10.

Subsequently, the procedure proceeds to ST 33. In ST 33, the infusion pump side profile data acquisition section (the program) 35 of FIG. 4 is operated so as to acquire the infusion pump side profile data in the infusion pump side profile data storage unit 104 of the infusion pump 100, thereby storing the data in the rack side infusion pump profile data storage unit 36.

Subsequently, the procedure proceeds to ST 34. In ST 34, a rack profile data comparison section (a program) 56 of FIG. 5 is operated so as to judge whether or not the rack side infusion pump profile data of the rack side infusion pump profile data storage unit 36 and the rack profile data of the rack profile data storage unit 55 are identical to each other.

In ST 34, when the two items of the profile data are not identical to each other, the process proceeds to ST 35. In ST 35, a third infusion pump side profile data rewriting section (a program) 57 of FIG. 5 is operated so as to rewrite the infusion pump side profile data in the infusion pump side profile data storage unit 104 of the infusion pump 100 into the rack profile data, for example, the ICU, thereby making a change. Accordingly, all of the infusion pumps 100 installed in the same rack device 10 are automatically unified with the same profile, for example, the ICU.

Therefore, it is possible to lighten the labor of the nurse or the like and to prevent the profile from, for example, being erroneously input by the nurse or the like. Thus, information of the drug library included in each infusion pump 100 can be effectively utilized.

However, the present invention is not limited to the above-described embodiments. The present embodiments have been described having an infusion pump 1 as an example of the equipment. However, without being limited thereto, the present invention can be preferably applied to other types of equipment of a liquid delivering apparatus or the like such as a syringe pump or the like.

What is claimed is:

1. A rack device on which a plurality of infusions pumps are mounted, each of the plurality of infusion pumps having, in a memory thereof, drug dosage information associated with drug usage location information, the rack device comprising:
    a rack control unit configured to control a first storage unit comprising a standard infusion pump judgment section and further configured to control a rack side communication device for communicating with each of the plurality of the infusion pumps,
    wherein each of the plurality of the infusion pumps comprises an infusion pump control unit to control an infusion pump side profile data storage unit, a display, and an input device and is configured to display the drug dosage information associated with the drug usage location information,
    wherein the infusion pump control unit is connected to the rack control unit through a bus, and
    wherein the rack control unit is configured to generate standard specifying drug usage location information based on drug usage location information stored in an infusion pump side profile data storage unit of a first infusion pump and cause a drug usage location information of each of the plurality of infusion pumps to automatically coincide with the standard specifying drug usage location information and store the standard specifying drug usage location information in an infusion pump side profile data storage unit of each of the plurality of infusion pumps, the first infusion pump being a first installed infusion pump installed on the rack device.

2. The rack device according to claim 1, wherein the rack control unit is further configured to detect a change in the drug usage location information stored in one of the plurality of infusion pumps to a post-change drug usage location information and cause the drug usage location information of each of the plurality of infusion pumps to coincide with the post-change drug usage location information.

3. The rack device according to claim 1, further comprising a plurality of installation portions, each of the plurality of installation portions receiving one of the plurality of infusion pumps.

4. A rack device on which a plurality of infusions pumps are mounted, each of the plurality of infusion pumps having, in a memory thereof, drug dosage information associated with drug usage location information, the rack device comprising:

a rack control unit configured to control a first storage unit comprising a rack position judgment section and further configured to control a rack side communication device for communicating with each of the plurality of the infusion pumps, wherein each of the plurality of infusion pumps comprises an infusion pump control unit to control an infusion pump side profile data storage unit, a display, and an input device and is configured to display the drug dosage information associated with the drug usage location information, wherein the infusion pump control unit is connected to the rack control unit through a bus, and wherein the rack control unit is configured to generate standard specifying drug usage location information based on drug usage location information stored in an infusion pump side profile data storage unit of a predetermined infusion pump and cause a drug usage location information of each of the plurality of infusion pumps to automatically coincide with the standard specifying drug usage location information and store the standard specifying drug usage location information in an infusion pump side profile data storage unit of each of the plurality of infusion pumps, the predetermined infusion pump being an infusion pump installed on a predetermined location on the rack device.

5. The rack control device according to claim 4, wherein the rack control unit is further configured to detect a change in the drug usage location information stored in one of the plurality of infusion pumps to a post-change drug usage location information and cause the drug usage location information of each of the plurality of infusion pumps to coincide with the post-change drug usage location information.

6. The rack control device according to claim 4, further comprising a plurality of installation portions, each of the plurality of installation portions receiving one of the plurality of infusion pumps.

7. The rack control device according to claim 6, wherein the predetermined infusion pump is an infusion pump installed in a predetermined one of the plurality of installation portions of the rack device.

8. The rack control device according to claim 7, wherein the predetermined one of the plurality of installation portions of the rack device is a top one of the plurality of installation portions.

* * * * *